United States Patent [19]

Beevor et al.

[11] Patent Number: 5,298,586
[45] Date of Patent: Mar. 29, 1994

[54] PROCESS FOR THE PRODUCTION OF CARBOXYLIC ACID ANHYDRIDES

[75] Inventors: Robert G. Beevor; Neil A. Greener; David J. Gulliver; Robert M. Sorrell, all of Hull, England

[73] Assignee: BP Chemicals Limited, London, England

[21] Appl. No.: 965,611

[22] Filed: Oct. 22, 1992

Related U.S. Application Data

[63] Continuation of Ser. No. 763,911, Sep. 23, 1991, abandoned.

[30] Foreign Application Priority Data

Oct. 23, 1990 [GB] United Kingdom ............ 90/21454.5

[51] Int. Cl.$^5$ .................. C07C 53/12; C07C 53/08
[52] U.S. Cl. ..................... 562/891; 562/607; 562/893
[58] Field of Search ............ 562/891, 893, 607

[56] References Cited

U.S. PATENT DOCUMENTS 4,430,273 2/1984 Erpenbach et al. .

FOREIGN PATENT DOCUMENTS

| 79461 | 5/1983 | European Pat. Off. . |
| 0087870 | 7/1983 | European Pat. Off. . |
| 0153834 | 9/1985 | European Pat. Off. . |
| 161874 | 11/1985 | European Pat. Off. . |
| 170965 | 8/1989 | European Pat. Off. . |
| 0391680 | 10/1990 | European Pat. Off. . |
| 1538783 | 1/1979 | United Kingdom . |

OTHER PUBLICATIONS

J. Chem. Soc. (1972) pp. 2616-2627.
Heterocyclic Chem., vol. 5, Potts Ed., pp. 352-353 (1985).
Organic & Biological Chem., Haake et al., 91:5, Feb. 26, 1969, pp. 1113-1119.
J. Chem. Soc. (1910), pp. 1814-1833.

Primary Examiner—José G. Dees
Assistant Examiner—B. Frazier
Attorney, Agent, or Firm—Brooks Haidt Haffner & Delahunty

[57] ABSTRACT

The solubility and stability of rhodium catalysts in rhodium-catalysed carbonylation of alkyl esters or alkyl ethers under substantially anhydrous conditions to produce carboxylic acid anhydrides is improved by the use of co-promoters selected from the group:

1,3-dialkyl-4-methylimidazolium iodide;
1,3-dialkyl-4-ethylimidazolium iodide;
1,3-dialkyl-4-n-propylimidazolium iodide;
1,3-dialkyl-4-isopropylimidazolium iodide;
1,3-dialkyl-4-n-butylimidazolium iodide
1,3-dialkyl-4-sec-butylimidazolium iodide
1,3-dialkyl-4-tert-butylimidazolium iodide;
1,3-dialkyl-2,4,5-trimethylimidazolium iodide and mixtures thereof where the alkyl groups are independently $C_1$ to $C_{20}$ alkyl.

11 Claims, No Drawings

PROCESS FOR THE PRODUCTION OF CARBOXYLIC ACID ANHYDRIDES

This application is a continuation of application Ser. No. 07/763,911 filed Sep. 23, 1991, now abandoned.

This invention relates to a carbonylation process and in particular to a rhodium-catalysed liquid phase carbonylation process for the production of carboxylic acid anhydrides.

Carbonylation processes are known in which small organic molecules such as alkenes, alkynes, alcohols, esters or ethers are reacted with carbon monoxide in the liquid phase and in the presence of a transition metal catalyst, for example rhodium. When esters or ethers are used as reactants carboxylic acid anhydrides can be produced. It is usual in such processes to use a halide promoter for the transition metal catalyst and often also a further co-promoter to stabilise the catalyst.

Thus, UK patent 1538783 describes a process for the preparation of an anhydride of a monocarboxylic acid which comprises reacting carbon monoxide, an iodide or bromide and a carboxylic ester and/or a hydrocarbyl ether, under substantially anhydrous conditions in the presence of a Group VIII noble metal catalyst and in the presence of a multiple promoter comprising at least one metal of Groups IVB, VB and VIB or a non-noble metal of Group VIII and an organo-nitrogen compound or an organo-phosphorus compound wherein the nitrogen and the phosphorus are trivalent.

According to GB 1538783 the organo-nitrogen co-promoter is preferably an amine, especially a tertiary amine of the formula:

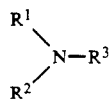

where $R^1$, $R^2$ and $R^3$ are the same or different and are alkyl, cycloalkyl, aryl or acyl groups which may be substituted by non-interfering groups preferably having up to 20 carbon atoms such as trimethylamine, triethylamine, triphenylamine or ethylenediamine tetraacetic acid or a heterocylic amine or an imidazole, such as imidazole or methyl imidazole or an imide of a carboxylic acid or a nitrile or amide or an oxime. The promoters are said to stabilize the catalyst and inhibit corrosion.

U.S. Pat. No. 4,430,273 describes a process for making acetic anhydride by reacting at least one substance selected from methyl acetate and dimethylether with carbon monoxide under substantially anhydrous conditions, at temperatures of 350 to 575K and under pressures of 1 to 300 bars in the presence of a catalyst system comprised of noble metals belonging to group VIII of the periodic system of the elements or their compounds and at least one substance selected from iodine and its compounds, which comprises using a promoter system consisting essentially of an aliphatic carboxylic acid with 1 to 8 carbon atoms and at least one heterocyclic aromatic compound, in which at least one hetero atom is a quaternary nitrogen atom.

According to U.S. Pat. No. 4,430,273 suitable promoters comprise:

(a) N-methylpyridinium iodide; N,N-dimethylimidazolium iodide; N-methyl-3-picolinium iodide; N-methyl-2,4-lutidinium iodide; N-methyl-3,4-lutidinium iodide; N-methyl-quinolinium iodide;

(b) pyridinium acetate; N-methylimidazolium acetate; 3-picolinium acetate; 2,4-lutidinium acetate; 3,4-lutidinium acetate.

Our published European patent application, EP 0153834 teaches the use of a thiol or an imidazole to stabilise the rhodium catalyst system and prevent loss by precipitation in a process for the liquid phase carbonylation of an alcohol, ester or ether by reaction with carbon monoxide in the presence of rhodium catalyst system comprising a rhodium component and an iodide or bromide component.

The imidazole is said to have the general formula:

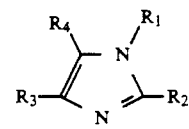

in which $R_1$, $R_2$, $R_3$ and $R_4$ are each independently hydrogen, alkyl, aryl, cycloalkyl or alkaryl hydrocarbyl radicals. A preferred imidazole is said to be N-methylimidazole and this is the only imidazole illustrated by experimental example.

With the use of such co-promoters there is sometimes a tendancy for precipitation and/or instability of the rhodium catalyst especially under unfavourable process conditions.

Our European patent application publication number EP 0391680A1 published after the priority date of the present application describes the use of certain selected quaternary ammonium iodides as catalyst stabilisers for rhodium catalysed carbonylation of an alcohol or its ester to a carboxylic acid in the presence of water. The catalyst stabilisers are selected from the group consisting of quaternary ammonium iodides having the formula:

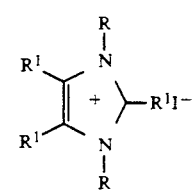  (1)

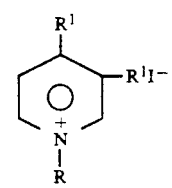  (2)

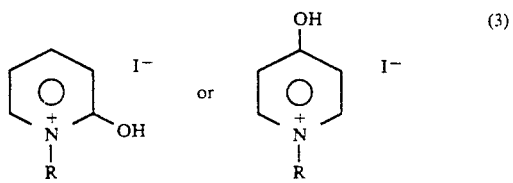  (3)

wherein the R and $R^1$ groups are independently selected from hydrogen or $C_1$ to $C_{20}$ alkyl groups with the proviso that at least one $R^1$ group is other than hydrogen.

According to EP 0391680A1 it is preferred that at least one of the R groups is the same as the $R^2$ group comprising the organic moiety of the alcohol, iodide derivative and carboxylic acid. The $R^1$ groups on the other hand are suitably hydrogen or $C_1$ to $C_8$ alkyl, preferably hydrogen or $C_1$ to $C_6$ alkyl with the proviso defined above. Examples of preferred catalyst stabilisers in each of classes (1) and (2) are said to be those where the $R^1$ groups are selected from hydrogen, methyl, ethyl, n-propyl, iso-propyl, n-butyl, sec-butyl and t-butyl.

One particularly preferred class of catalyst stabilisers is said to be iodide salts of the cation:

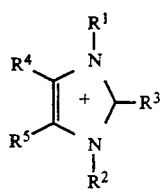

Where
(i) $R^1$ and $R^2$ are methyl
(ii) $R^5$ is hydrogen
(iii) $R^3$ is $C_1$ to $C_{20}$ alkyl or hydrogen
and
(iv) $R^4$ is $C_1$ to $C_{20}$ alkyl.

Most preferred examples of this class are said to be where (1) $R^3=C_2H_5$, $R^1$, $R^2$ and $R^4=CH_3$ and $R^5=H$ or (2) $R^3$ and $R^5=H$, and $R^1$, $R^2$ and $R^4=CH_3$.

The carbonylation process of EP 0391680 A1 differs from that of the present invention in that it produces carboxylic acids from alcohols or their esters in the presence of a finite amount of water in the reactor. The process of the present invention on the other hand produces carboxylic acid anhydrides from esters and/or ethers substantially in the absence of water in the reactor.

The technical problem to be solved by the present invention is to provide a co-promoter for rhodium-catalysed liquid phase carbonylation processes for the production of carboxylic acid anhydrides under substantially anhydrous conditions which reduces the tendancy for precipitation and/or instability of the rhodium catalyst.

Thus according to the present invention there is provided a process for the production of a carboxylic acid anhydride comprising reacting in a reaction zone under substantially anhydrous conditions, carbon monoxide with a carboxylic acid ester or an alkyl ether in the presence of a rhodium catalyst, an iodide promoter and a co-promoter characterised in that the co-promoter is selected from the group consisting of 1,3-dialkyl-4-methylimidazolium iodide; 1,3-dialkyl-4-ethylimidazolium iodide; 1,3-dialkyl-4-n-butylimidazolium iodide; 1,3-dialkyl-4-sec-butylimidazolium iodide; 1,3-dialkyl-4-tert.-butyl imidazolium iodide; 1,3-dialkyl-4-n-propylimidazolium iodide; 1,3-dialkyl-4-isopropylimidazolium iodide; 1,3-dialkyl-2,4,5-trimethylimidazolium iodide and mixtures thereof where the alkyl groups are independently $C_1$ to $C_{20}$ alkyl, preferably methyl or ethyl, more preferably methyl.

The present invention solves the problem defined above by using certain selected quaternary ammonium iodides which have been shown not to generate sparingly soluble rhodium containing complexes even under severe conditions which have been designed to exacerbate rhodium catalyst instability.

By substantially anhydrous conditions in the reaction zone is meant a complete absence of water or a water concentration of less than 0.1% by weight.

The process of the present invention may be operated as a batch or a continuous process, preferably a continuous process. When operated as a continuous process, reaction medium may be continuously removed from the reaction zone and the carboxylic acid anhydride separated therefrom prior to recycle of the catalyst and promoters to the reaction zone. It is during such separation of catalyst and promoters from the reaction medium for example, that rhodium catalyst precipitation can occur due to, for example, a deficiency of carbon monoxide relative to the reaction zone. It is believed that the co-promoter of the present invention can provide improved solubility and stability of the rhodium catalyst in such separations and hence allow for increased productivity and/or reaction at more moderate conditions.

The carboxylic acid ester and alkyl ether preferably have 2 to 6 carbon atoms. Preferred reactants are methyl acetate, ethyl acetate and dimethyl ether. A controlled amount of alkanol, for example methanol or ethanol, and/or water may be introduced to the reaction zone with the carboxylic acid ester and/or alkyl ether feedstock to coproduce carboxylic acid, provided that substantially anhydrous conditions are maintained in the reaction zone. Thus, for example, a controlled amount of methanol and/or water may be introduced to the reaction zone with methyl acetate to coproduce acetic acid with acetic anhydride, provided that substantially anhydrous conditions are maintained in the reaction zone.

Any soluble rhodium containing catalyst useful in the carbonylation of esters or ethers may be used herein. The source of rhodium may be, for example, a simple inorganic salt such as rhodium chloride, bromide, iodide, or nitrate; a carbonyl or organometallic complex of rhodium, or a coordination complex. Finely divided rhodium metal which becomes solubilised in the reaction medium may also be used.

The iodide promoter used in conjunction with the catalyst may be added as elemental iodine, hydrogen iodide, an iodide salt, for example sodium iodide, or an organic source of iodide such as an alkyl or aryl iodide. A preferred source of the iodide component is methyl iodide. It is possible to supply part of the iodide with the rhodium by using, for example, a compound such as rhodium triiodide. The concentration of iodide is such as to produce a rhodium to iodide molar ratio of at least 1:4 preferably between 1:10 and 1:1000.

The co-promoter is present in amounts such that the molar ratio of co-promoter to rhodium catalyst is at least 0.5:1 and preferably in the range 0.5:1 to $10^5$:1. The co-promoters of the present invention may be prepared separately before being introduced to the reaction zone or they may be prepared in situ by, for example, a corresponding imidazole being quaternised by a source of alkyl iodide in situ. The imidazole itself, may also be prepared in situ by alkylation of a less substituted imidazole by a source of alkyl iodide such as methyl iodide.

The carbonylation reaction as described herein is carried out in the liquid phase comprising a solution of the catalyst system. The concentration of the soluble rhodium component will in general be such as to constitute between 10 ppm and 20000 ppm preferably between 10 ppm and 10000 ppm and most preferably between 10 ppm and 3000 ppm of the reaction mixture.

The process is carried out under superatmospheric pressure and at elevated temperature. Although the optimum conditions will depend on the particular feedstock and catalyst system used, the reaction is generally carried out at a pressure of greater than 10 bars, preferably 10 to 100 bars and at a temperature in the range of 100° to 250° C. For the preferred feedstocks mentioned herein, the optimum temperature and pressure range will vary somewhat. However, the ranges of such optimum temperatures and pressure for a given feedstock will be familiar to those skilled in the art of carbonylation.

It is preferable that the carbon monoxide used in this invention is as pure as possible. However, a certain amount of diluent gases such as nitrogen or gases which are often co-produced with carbon monoxide, such as hydrogen, may be present. If hydrogen is present it should be at a level consistent with the desired level of by-products which may be produced therefrom. Preferably, hydrogen is present in the reaction zone, at a partial pressure suitably 0.01 to 10 bara, preferably 0.1 to 3 bara.

A suitable continuous process for the present invention is described in our European patent application EP 0087870A, which describes a process for the production of acetic anhydride with or without the net co-production of acetic acid from methanol and carbon monoxide in a series of esterification, carbonylation and separation steps comprising (1) reacting methanol with recycle acetic acid in an esterification step to form an esterification product containing predominantly methyl acetate, water and optionally unreacted methanol; (2) removing part of the water from the esterification product; (3) reacting the esterification product still containing water with carbon monoxide in a carbonylation step in the presence as catalyst of free or combined metallic carbonylation catalyst and as promoter of free or combined halogen to form a carbonylation product containing acetic acid and acetic anhydride; (4) separating the carbonylation product by fractional distillation into a low boiling fraction containing carbonylation feed and volatile carbonylation promoter components, acetic acid and acetic anhydride fractions, and a higher boiling fraction containing carbonylation catalyst components; (5) recycling the low boiling fraction containing carbonylation feed and carbonylation promoter components and the higher boiling fraction containing carbonylation catalyst components to the carbonylation step; and (6) recycling at least part of the acetic acid fraction to the esterification step.

The solubilising and stabilising influence of the co-promoters of the present invention will now be illustrated by way of the following examples.

Preparation of Rhodium Catalyst Stock Solution

A mixture of rhodium triiodide (6.28 g, 13.00 mmol), water (28.0 g), HI (4.0 g of a 57% aqueous solution) and glacial acetic acid (134.0 g) was introduced into a 300 ml Hastelloy B2 autoclave. The autoclave was sealed and charged to 30 barg with carbon monoxide and heated to 180° C. and maintained at this temperature for 48 hours. At the end of this period the autoclave was cooled and vented. The solution was centrifuged and analysed for rhodium concentration by acid digestion followed by atomic absorption spectroscopy. Typically the catalyst stock solution contained between 2000–3000 ppm rhodium. The stock solution was filtered before use.

Preparation of the Quaternised Imidazoles

The quaternised imidazoles according to and not according to the present invention were prepared by treatment of a respective imidazole in tetrahydrofuran with 3 to 4 equivalents of methyl iodide followed by reflux for twelve hours. In some cases the imidazole was alkylated as well as quaternised by the methyl iodide. The quaternised imidazoles and corresponding imidazoles are summarised below. The products isolated from these reactions were further treated with methyl iodide in an acetic acid, acetic anhydride, methyl acetate mixture at 180° C. in a Fischer-Porter tube in the first stage of the solubility/stability test to ensure complete quaternisation of the imidazole.

EXAMPLES ACCORDING TO PRESENT INVENTION

| Quaternised Imidazole | Imidazole |
| --- | --- |
| 1,3,4-trimethylimidazolium iodide | 4-methyl imidazole |
| 1,2,3,4,5-pentamathylimidazolium iodide | 1,2,4,5-tetramethyl imidazole |
| Comparative Experiments | |
| Quaternised Imidazole | Imidazole |
| 1,3-dimethylimidazolium iodide | 1-methyl imidazole |
| 1,2,3-trimethylimidazolium iodide | 1,2-dimethyl imidazole |

The imidazoles were supplied by commercial sources.

Solubility and Stability Measurements

Examples According to the Present Invention

EXAMPLE 1

3.62 g of 1,3,4-trimethylimidazolium iodide prepared as described above was added to a solution of acetic anhydride (3.33 g), methyl acetate (2.38 g), methyl iodide (2.85 g) and acetic acid (5.11 g). The mixture was then heated in a Fischer-Porter tube for 12 hours at 180° C. under 1 bara nitrogen. At the end of this period the solution was cooled to room temperature and 2.95 g of the catalyst stock solution added. The solution was stirred for one hour at room temperature and then sampled. The sample solution was centrifuged and the solution analysed for rhodium by acid digestion followed by atomic absorption spectroscopy to provide a measure of the solubility of the rhodium catalyst in the presence of the co-promoter.

The remaining solution was heated to 180° C. under 1 bara nitrogen for 22 hours. At the end of this period the solution was cooled and sampled. The sample solution was centrifuged and the solution analysed for rhodium by acid digestion followed by atomic absorption spectroscopy to provide a measure of the stability of the rhodium catalyst in the presence of the co-promoter. The results are shown in Table 1.

EXAMPLE 2

3.59 g of 1,2,3,4,5-pentamethylimidazolium iodide prepared as described above was added to a solution of acetic anhydride (3.31 g), methyl acetate (2.38 g), methyl iodide (2.67 g) and acetic acid (5.12 g). The mixture was then heated in a Fischer-Porter tube for 12 hours at 180° C. under 1 bara nitrogen. At the end of this period the solution was cooled to room temperature and 3.00 g of the catalyst stock solution added. The solution was stirred for one hour at room temperature and then sampled. The sample solution was centrifuged and the solution analysed for rhodium by acid digestion followed by atomic absorption spectroscopy to provide a measure of the rhodium solubility in the presence of the co-promoter.

The remaining solution was heated to 180° C. under 1 bara nitrogen for 22 hours. At the end of this period the solution was cooled and sampled. The sample solution was centrifuged and the solution analysed for rhodium by acid digestion followed by atomic absorption spectroscopy to provide a measure of the stability of the rhodium catalyst in the presence of the co-promoter. The results are shown in Table 1.

Comparative Experiments

Comparative Experiment A 3.61 g of 1,2,3-trimethylimidazolium iodide prepared as described above was added to a solution of acetic anhydride (3.31 g), methyl acetate (2.38 g), methyl iodide (2.86 g) and acetic acid (5.11 g). The mixture was then heated in a Fischer-Porter tube for 12 hours at 180° C. under 1 bara nitrogen. At the end of this period the solution was cooled to room temperature and 3.00 g of the catalyst stock solution added. The solution was stirred for one hour at room temperature and then sampled. The sample solution was centrifuged and the solution analysed for rhodium by acid digestion followed by atomic absorption spectroscopy to provide a measure of the solubility of the rhodium catalyst in the presence of the co-promoter.

The remaining solution was heated to 180° C. under 1 bara nitrogen for 22 hours. At the end of this period the solution was cooled and sampled. The sample solution was centrifuged and the solution analysed for rhodium by acid digestion followed by atomic absorption spectroscopy to provide a measure of the stability of the rhodium catalyst in the presence of the co-promoter. The results are shown in Table 1.

Comparative Experiment B 3.65 g of 1,3-dimethylimidazolium iodide prepared as described above was added to a solution of acetic anhydride (3.30 g), methyl acetate (2.40 g), methyl iodide (2.89 g) and acetic acid (5.13 g). The mixture was then heated in a Fischer-Porter tube for 12 hours at 180° C. under 1 bara nitrogen. At the end of this period the solution was cooled to room temperature and 2.89 g of the catalyst stock solution added. The solution was stirred for one hour at room temperature and then sampled. The sample solution was centrifuged and the solution analysed for rhodium by acid digestion followed by atomic absorption spectroscopy to provide a measure of the solubility of the rhodium catalyst in the presence of the co-promoter.

The remaining solution was heated to 180° C. under 1 bara nitrogen for 22 hours. At the end of this period the solution was cooled and sampled. The sample solution was centrifuged and the solution analysed for rhodium by acid digestion followed by atomic absorption spectroscopy to provide a measure of the stability of the rhodium catalyst in the presence of the co-promoter. The results are shown in Table 1.

TABLE 1

| | Rhodium Solubility (ppm) | Rhodium Stability (ppm) |
| --- | --- | --- |
| Experiment 1 | 317 | 324 |
| Experiment 2 | 298 | 308 |
| Comparative Experiment A | 40 | 42 |
| Comparative Experiment B | 36 | 70 |

Note: The results in Table 1 have been corrected for small unavoidable losses of volatile components during the experiments.

EXAMPLES 4 AND 5 AND COMPARATIVE EXPERIMENTS C & D

Further experiments were performed using increased amounts of acetic anhydride.

Preparation of Quaternised Imidazoles

Quaternised imidazoles were prepared by treating the respective free base in dichloromethane with 3–4 equivalents of methyl iodide followed by heating to reflux for three hours. The product was isolated by removal of the solvent in vacuo.

Comparative Experiment C 1,3-dimethylimidazolium iodide (2.789 g) prepared as described above was added to a solution of acetic anhydride (4.205 g), acetic acid (11.511 g), methyl iodide (3.111 g) and methyl acetate (3.001 g). The mixture was then heated in a Fischer-Porter vessel for 12 hours at 180° C. under 1 bara nitrogen. At the end of this period the solution was allowed to cool to room temperature and [Rh(CO)$_2$Cl]$_2$ (0.0305 g) added. The solution was stirred for one hour at room temperature and sampled. The sample solution was centrifuged and the solution analysed for rhodium by acid digestion followed by atomic absorption spectroscopy to provide a measure of the solubility of the rhodium catalyst in the presence of the co-promoter.

The remaining solution was heated to 180° C. under 1 bara of nitrogen for 12 hours. At the end of this period the solution was cooled and sampled. The sample solution was centrifuged and the solution analysed for rhodium by acid digestion followed by atomic absorption spectroscopy to provide a measure of the stability of the rhodium catalyst in the presence of co-promoter. The results are shown in Table 2.

EXAMPLE 4

1,3,4-trimethylimidazolium iodide (2.368 g) prepared as described above was added to a solution of acetic anhydride (4.215 g), acetic acid (10.629 g), methyl iodide (3.223 g) and methyl acetate (3.210 g). The mixture was then heated in a Fischer-Porter vessel for 12 hours at 180° C. under 1 bara nitrogen. At the end of this period the solution was allowed to cool to room temperature and ]Rh(CO)$_2$Cl]$_2$ (0.0298 g) was added. The solution was stirred for one hour at room temperature and sampled. The sample solution was centrifuged and the solution analysed for rhodium by acid digestion followed by atomic absorption spectroscopy to provide a measure of the solubility of the rhodium catalyst in the presence of the co-promoter.

The remaining solution was heated to 180° C. under 1 bara of nitrogen for 12 hours. At the end of this period the solution was cooled and sampled. The sample solution was centrifuged and the solution analysed for rhodium by acid digestion followed by atomic absorption spectroscopy to provide a measure of the stability of the rhodium catalyst in the presence of co-promoter. The results are shown in Table 2.

EXAMPLE 5

1,2,3,4,5-pentamethylimidazolium iodide (2.444 g) prepared as described above was added to a solution of acetic anhydride (4.215 g), acetic acid (10.991 g), methyl iodide (3.330 g) and methyl acetate (3.006 g). The mixture was then heated in a Fischer-Porter vessel for 12 hours at 180° C. under 1 bara nitrogen. At the end of this period the solution was allowed to cool to room temperature and [Rh(CO)$_2$Cl]$_2$ (0.0337 g) was added. The solution was stirred for one hour at room temperature and sampled. The sample solution was centrifuged and the solution analysed for rhodium by acid digestion followed by atomic absorption spectroscopy to provide a measure of the solubility of the rhodium catalyst in the presence of the co-promoter.

The remaining solution was heated to 180° C. under 1 bara of nitrogen for 12 hours. At the end of this period the solution was cooled and sampled. The sample solution was centrifuged and the solution analysed for rhodium by acid digestion followed by atomic absorption spectroscopy to provide a measure of the stability of the rhodium catalyst in the presence of co-promoter. The results are shown in Table 2.

TABLE 2

|  | Rhodium Solubility (ppm) | Rhodium Stability (ppm) |
| --- | --- | --- |
| Comparative Experiment D | 35 | 66 |
| Example 4 | 235 | 877 |
| Example 5 | 335 | 813 |

Notes:
(1) The results have been corrected to allow for small unavoidable loss of volatile components during the experiment.
(2) The stability concentrations are higher than the solubility concentrations due to increased dissolution on heating.

The results in Table 2 show that under adverse conditions the co-promoters according to the present invention support a higher concentration of rhodium in solution than other co-promoters.

Carbonylation Reaction Experiments

Preparation of Quaternised Imidazole—Experiment 6

1,2,4,5-tetramethylimidazole was treated with 3 to 4 molar equivalents of methyl iodide in dichloromethane solvent and refluxed for three hours. The solvent was then removed by vacuum to yield 1,2,3,4,5-pentamethylimidazolium iodide which was used in the subsequent carbonylation reaction. Carbonylation Reaction in Presence of 1,2,3,4,5-Pentamethylimidazolium Iodide—Experiment 7

1,2,3,4,5-pentamethylimidazolium iodide (9.02 g) prepared as above; acetic anhydride (5.21 g); methyl acetate (6.81 g); methyl iodide (7.96 g); acetic acid (21.01 g) and [Rh(CO)$_2$Cl]$_2$ (0.072 g) (equivalent to 761 ppm rhodium in the reactor contents) was charged to a 100 ml Hastalloy B2 autoclave. The autoclave was sealed and presurised to 4 bar gauge with carbon monoxide and heated to 180° C. When a steady temperature had been obtained, the pressure was raised to 41 bar by the addition of further carbon monoxide. The temperature was maintained for 1 hour during which time the uptake of carbon monoxide was measured by pressure fall. At the end of this period the autoclave was cooled and depressurised and the contents analysed by gas chromatography. Yield of acetic anhydride was 3.31 g corresponding to a 35.2% conversion of methyl acetate. Reaction rate based upon carbon monoxide uptake was 3.35 mol/kg/h.

We claim:
1. A process for the production of a carboxylic acid anhydride comprising reacting in a reaction zone under substantially anhydrous conditions, carbon monoxide with a carboxylic acid ester or an alkyl ether in the presence of a rhodium catalyst, an iodide promoter and a co-promoter, and separating the carboxylic acid anhydride product from the rhodium catalyst and promoters under conditions deficient of carbon monoxide relative to the reaction zone, in which process the co-promoter is selected from the group consisting of:
1,3-dialkyl-4-methylimidazolium iodide
1,3-dialkyl-4-ethylimidazolium iodide
1,3-dialkyl-4-n-propylimidazolium iodide
1,3-dialkyl-4-isopropylimidazolium iodide
1,3-dialkyl-4-n-butylimidazolium iodide
1,3-dialkyl-4-sec-butylimidazolium iodide
1,3-dialkyl-4-tert-butylimidazolium iodide
1,3-dialkyl-2,4,5-trimethylimidazolium iodide and mixtures thereof where the alkyl groups are independently C1 to C20 alkyl.

2. A process as claimed in claim 1 in which the alkyl groups of the co-promoter are methyl or ethyl.

3. A process as claimed in claim 1 in which the copromoter is selected from the group consisting of:
1,3,4-trimethylimidazolium iodide; and
1,2,3,4,5-pentamethylimidazolium iodide;

4. A process as claimed in claim 1 in which the co-promoter is prepared in situ by quaternising a corresponding imidazole with an alkyl iodide.

5. A process as claimed in claim 4 in which the corresponding imidazole is prepared in situ by alkylating a less substituted imidazole by an alkyl iodide.

6. A process as claimed in claim 1 in which the process is operated continuously with removal of reaction medium from the reaction zone and with separation from the reaction medium of the carboxylic acid anhydride product prior to recycle of the rhodium catalyst and promoters to the reaction zone.

7. A process as claimed in claim 1 in which the carboxylic acid ester or alkyl ether has from 2 to 6 carbon atoms.

8. A process as claimed in claim 7 in which the carboxylic acid ester is methyl acetate or ethyl acetate.

9. A process as claimed in claim 1 in which the co-promoter is present in a molar ratio to the rhodium catalyst of from 0.5:1 to 10$^5$:1.

10. A process for the production of a carboxylic acid anhydride comprising reacting in a reaction zone carbon monoxide with a carboxylic acid ester or an alkyl ether in the presence of a rhodium catalyst, an iodide promoter and a co-promoter, and separating the carboxylic acid anhydride product from the rhodium catalyst and promoters under conditions deficient of carbon monoxide relative to the reaction zone, in which process the co-promoter is selected from the group consisting of:
1,3-dialkyl-4-methylimidazolium iodide
1,3-dialkyl-4-ethylimidazolium iodide
1,3-dialkyl-4-n-propylimidazolium iodide
1,3-dialkyl-4-isopropylimidazolium iodide
1,3-dialkyl-4-n-butylimidazolium iodide
1,3-dialkyl-4-sec-butylimidazolium iodide
1,3-dialkyl-4-tert-butylimidazolium iodide
1,3-dialkyl-2,4,5-trimethylimidazolium iodide
and mixtures thereof where the alkyl groups are independently $C_1$ to $C_{20}$ alkyl; and further comprising introducing a controlled amount of alkanol, water, or mixture thereof to the reaction zone with the carboxylic acid ester or alkyl ether feedstock to coproduce a carboxylic acid.

11. A process as claimed in claim 10 in which a controlled amount of methanol, water, or mixture thereof is introduced to the reaction zone with methyl acetate to coproduce acetic acid with acetic anhydride.

* * * * *

UNITED STATES PATENT AND TRADEMARK OFFICE
CERTIFICATE OF CORRECTION

PATENT NO. : 5,298,586

DATED : March 29, 1994

INVENTOR(S) : Robert G. Beevor, et al

It is certified that error appears in the above-indentified patent and that said Letters Patent is hereby corrected as shown below:

Column 2, line 45, correct the structural formula to read:

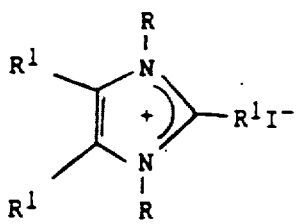

Column 3, line 18, correct the sturctural formula to read:

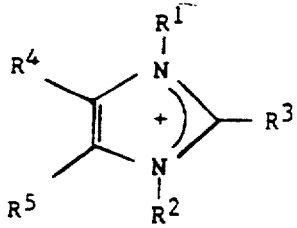

Column 6, line 25, correct the spelling of the word "pentamethylimidazolium"

Column 6, line 28, correct the spelling of the word "Quaternised"

Column 8, line 54, change "(4.215g)" to —(4.223g)—

Column 9, lines 58-59, the title for "Experiment 7" should be presented as "Carbonylation Reaction in Presence of"

UNITED STATES PATENT AND TRADEMARK OFFICE
CERTIFICATE OF CORRECTION

PATENT NO. : 5,298,586

DATED : March 29, 1994

INVENTOR(S) : Robert G. Beevor, et al

It is certified that error appears in the above-indentified patent and that said Letters Patent is hereby corrected as shown below:

Column 10, claim 1, lines 32-33 should read as a single line
Column 10, claim 3, last line, change the semi-colon "(;)" to a period (.).

Signed and Sealed this

Twenty-third Day of August, 1994

Attest:

BRUCE LEHMAN

Attesting Officer

Commissioner of Patents and Trademarks